(12) United States Patent
Hussain et al.

(10) Patent No.: US 6,608,073 B1
(45) Date of Patent: Aug. 19, 2003

(54) INTRANASAL CODEINE FOR THE RAPID SUPPRESSION OF COUGH AND RAPID RELIEF OF PAIN

(75) Inventors: Anwar A. Hussain, Lexington, KY (US); Lewis W. Dittert, Lexington, KY (US); Abeer M. Al-Ghananeem, Lexington, KY (US)

(73) Assignee: New Millennium Pharmaceutical Research, Inc., Lexington, KY (US)

( * ) Notice: Subject to any disclaimer, the term of this patent is extended or adjusted under 35 U.S.C. 154(b) by 0 days.

(21) Appl. No.: 09/410,033

(22) Filed: Oct. 1, 1999

Related U.S. Application Data

(60) Provisional application No. 60/104,272, filed on Oct. 14, 1998.

(51) Int. Cl.[7] .............................................. A61K 31/435
(52) U.S. Cl. ...................... 514/277; 514/279; 514/280; 514/282; 424/43; 424/434
(58) Field of Search ................... 514/277, 279, 514/280, 282; 424/43, 434

(56) References Cited

U.S. PATENT DOCUMENTS

| | | | | |
|---|---|---|---|---|
| 4,534,974 A | | 8/1985 | Kim ........................... 514/161 |
| 4,683,235 A | * | 7/1987 | Hynes ......................... 514/282 |
| 5,025,019 A | * | 6/1991 | Sunshine et al. ............ 514/277 |
| 5,116,847 A | | 5/1992 | Gilbert et al. |
| 5,164,398 A | * | 11/1992 | Sims et al. .................. 514/282 |
| 5,173,304 A | | 12/1992 | Löhner et al. ............... 424/456 |
| 5,362,498 A | | 11/1994 | Aiache ........................ 424/435 |
| 5,468,744 A | | 11/1995 | Raffa et al. .................. 514/282 |
| 5,629,011 A | | 5/1997 | Illum ........................... 424/434 |
| 5,753,651 A | * | 5/1998 | dePadova ................. 514/223.5 |

FOREIGN PATENT DOCUMENTS

| | | |
|---|---|---|
| EP | 0388125 | 9/1990 |
| EP | 0535841 | 4/1993 |
| WO | WO 93/15737 | 8/1993 |
| WO | 96/05834 | 2/1996 |
| WO | WO 98/42275 | 10/1998 |

OTHER PUBLICATIONS

Goodman & Gilman's The Pharmacological Basis of Therapeutics, Ninth Edition (1996), p. 539.*
J.M. Alexander–Williams et al., "Novel Routes of Opioid Adminstration" *British Journal of Anaesthesia* 81: 3–7 (1998).

* cited by examiner

*Primary Examiner*—Dwayne C. Jones
*Assistant Examiner*—C. Delacroix-Muirheid
(74) *Attorney, Agent, or Firm*—Burns, Doane, Swecker & Mathis, LLP

(57) ABSTRACT

This invention provides a method of rapidly and reliably delivering codeine, alone or in combination with other compounds, to the systemic circulation by administration via the nasal route to produce rapid onset of beneficial effects in the treatment of pain or cough. The present invention further provides pharmaceutical compositions comprising codeine, and/or pharmaceutically acceptable salts thereof in a variety of unique pharmaceutical dosage forms, with and without other analgesic and/or antitussive compounds.

21 Claims, 2 Drawing Sheets

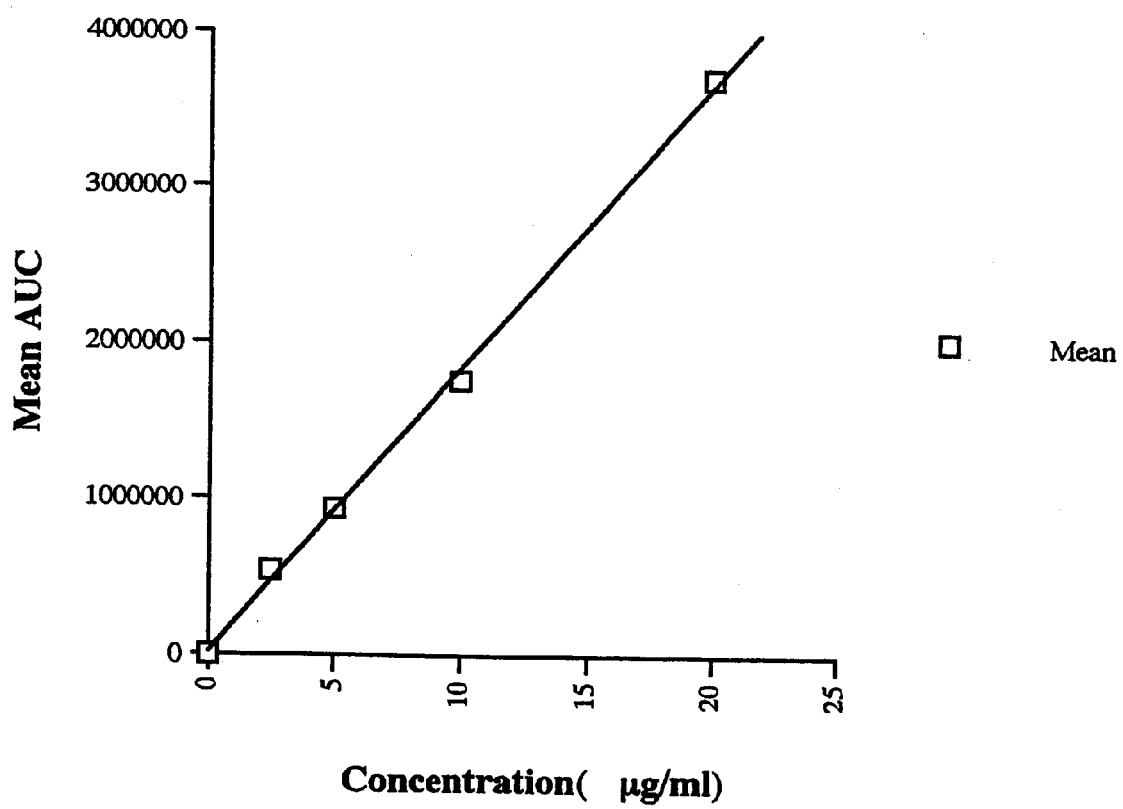

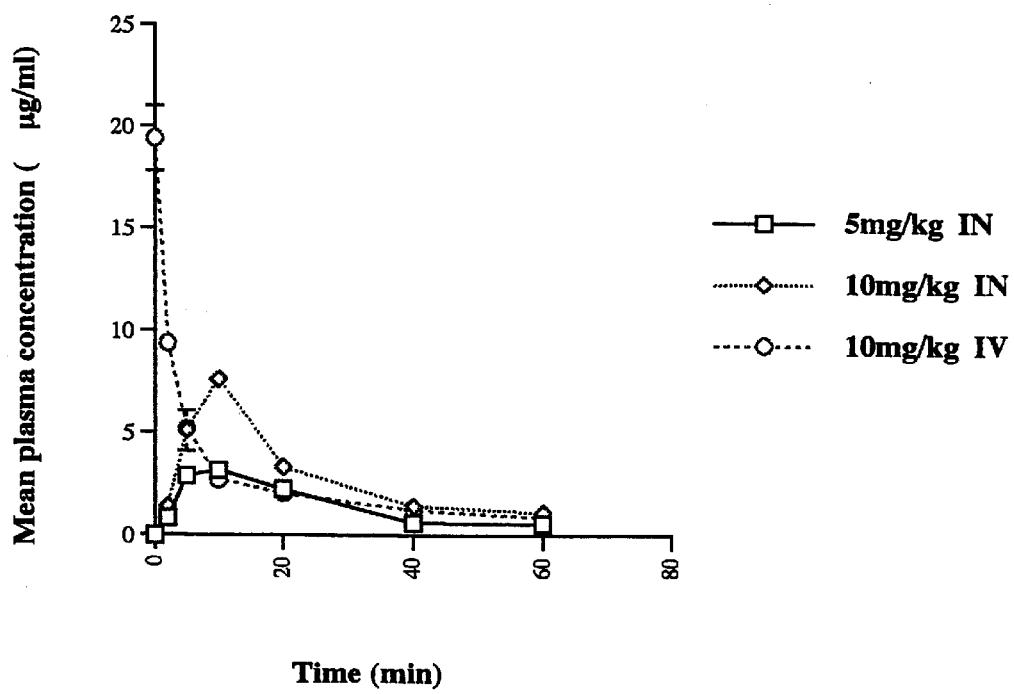
Figure 2 : Mean plasma codiene concentration ( µg/ml) vs time (minutes) following nasal and intravenous administration.

INTRANASAL CODEINE FOR THE RAPID SUPPRESSION OF COUGH AND RAPID RELIEF OF PAIN

This application claims priority under 35 U.S.C. §119 (e) to provisional application No. 60/104,272, filed in the United States Patent and Trademark Office on Oct. 14, 1998.

BACKGROUND OF THE INVENTION

1. Field of the Invention

This invention relates to a method for greatly accelerating the rate of delivery of codeine, and derivatives thereof, to the central nervous system by administration via the nasal route to provide extremely rapid response in the prevention or treatment of pain or relief of cough in a patient in need of such prevention or treatment. This invention relates to a method for greatly accelerating the rate of delivery of codeine, and derivatives thereof, to the central nervous system by administration via the nasal route to provide extremely rapid response in the prevention or treatment of cough in a patient in need of such prevention or treatment. This method also provides for direct absorption of codeine into the central nervous system, bypassing the metabolic enzymes circulating in the bloodstream that would otherwise destroy codeine administered by another route.

2. Description of the Related Art

Opioid analgesics are the most potent pain-relieving drugs currently available. Furthermore, of all analgesics, they have the broadest range of efficacy, providing the most reliable method for rapidly relieving pain. However, side effects, including respiratory depression, are common.

Opioids produce analgesia by actions in the central nervous system. They activate pain-inhibitory neurons and directly inhibit pain-transmission neurons. Most of the commercially available opioid analgesics act at the same opiate receptor (the $\mu$receptor), differing mainly in potency, speed of onset, duration of action, and optimal route of administration.

Opioid compounds also have antitussive (i.e., cough-suppressant) effects, via their direction action on the neural cough-control center in the medulla. Cough suppression often occurs with lower doses than those needed for analgesia. For example, an oral dose of 30 to 60 mg of codeine is typically required to produce analgesia. However, a 10- or 20-mg oral dose of codeine, although ineffective for analgesia, produces a demonstrable antitussive effect. Higher doses of codeine produce even more suppression of chronic cough.

The most rapid relief with opioids is obtained by IV administration; relief with oral administration is significantly slower. Common side effects include nausea, vomiting, sedation, and constipation. These effects are dose-related, and there is great variability among patients in the doses that relieve pain and produce side effects. Because of this, initiation of therapy requires titration to optimal dose and interval.

Codeine (methyl morphine) is an opioid compound chemically closely related to morphine, but with only one-twentieth of the narcotic action, and one-third the antitussive activity, of morphine. In contrast to morphine, codeine is approximately 60% as effective orally as parenterally, both as an analgesic and as a respiratory depressant. Very few opioids have so high an oral-parenteral potency ratio. The greater oral efficacy of codeine is due to less first-pass metabolism in the liver. Once absorbed, codeine is metabolized by the liver and excreted chiefly in the urine, largely in inactive forms. A small fraction (approximately 10%) of administered codeine is demethylated to form morphine, and both free and conjugated morphine can be found in the urine after therapeutic doses of codeine. Codeine has an exceptionally low affinity for opioid receptors, and much of the analgesic effect of orally-administered codeine is likely due to its conversion to morphine. However, its antitussive actions probably involve distinct receptors that bind codeine itself. The half-life of codeine in plasma is 2 to 4 hours.

SUMMARY OF THE INVENTION

A major object of the present invention is to provide a method for safely and conveniently administering codeine to a patient in need of treatment of pain, in order to produce a rapid and reliable response in less time than current dosage forms. The method comprises the intranasal administration of an effective amount of codeine to a patient suffering from pain.

A further object of the present invention is to provide a method for safely and conveniently administering codeine to a patient in need of treatment of cough, in order to produce a rapid and reliable response in less time than current dosage forms. The method comprises the intranasal administration of an effective amount of codeine to a patient suffering from uncontrolled cough.

The objective of the present invention is to improve the rate of delivery of codeine to the central nervous system by administering codeine via the nasal route in order to speed the onset of effect and reduce the dose required for its beneficial effect. Intranasal delivery will improve drug bioavailability by direct absorption into the central nervous system, thereby avoiding extensive first-pass metabolism which may significantly lower the plasma concentrations of codeine when it is administered via another route. Also, intranasal delivery will produce less constipation than the oral route. As a result, small doses of codeine, or derivatives thereof, can be administered which will result in fewer side effects, and the drug will be more tolerable and more effective in patients suffering from pain or cough. Importantly, since codeine is rapidly effective following intranasal administration, establishment of an ideal dose for a particular patient is greatly facilitated.

Intranasal dosage forms containing codeine in combination with other drugs used in the treatment of pain and/or chronic cough may also be employed in the practice of the present invention. Such additional drugs include, but are not limited to, opioid and/or nonopioid analgesics, and opioid and/or nonopioid antitussives.

With the foregoing and other objects, advantages and features of the invention that will become hereinafter apparent, the nature of the invention is further explained in the following detailed description of the preferred embodiments of the invention and in the appended claims.

BRIEF DESCRIPTION OF THE DRAWINGS

FIG. 1 is the standard curve for the HPLC used in the experiments described in Example 4, below.

FIG. 2 shows the change in mean plasma concentration of codeine over time following intranasal or intravenous administration.

DETAILED DESCRIPTION OF THE PREFERRED EMBODIMENTS OF THE INVENTION

Thus, the present inventors have discovered a novel method for the delivery of codeine, or derivatives thereof, to a patient in need of such treatment, comprising the intranasal administration of codeine. This method offers significant clinical advantages over the prior art.

More specifically, the inventors sought to provide a rapid, reliable, safe, effective and convenient treatment for pain or cough comprising administering codeine to a patient in need of such treatment, which comprises the administration of codeine intranasally, thus providing rapid response compared to prior art methods of treatment of pain or cough while avoiding the side-effects associated with oral dosage forms. Specifically, smaller doses of codeine can be administered through the nasal route, thus resulting in fewer side effects. By using the method of the present invention, which produces an rapid response, the drug will become more tolerable and more effective in treating patients suffering from pain or cough.

More particularly, the present invention concerns the intranasal administration of codeine, which has the chemical structure of formula (I):

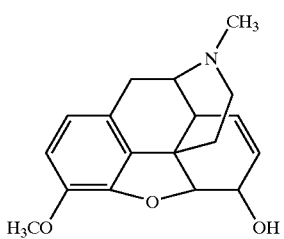

(I)

or a pharmaceutically acceptable salt thereof, or a pharmaceutical composition containing said compound. Preferred pharmaceutically acceptable salts of codeine for use in the present invention include, but are not limited to, codeine sulfate and codeine phosphate. Such pharmaceutical compositions may be a medicament for the treatment of pain in an animal, particularly a mammal, including a human. Alternatively, such pharmaceutical compositions may be a medicament for the treatment of cough in an animal, particularly a mammal, including a human.

The present inventors have found that intranasal administration of codeine effectively results in complete and very rapid absorption of these compounds into the central nervous system (CNS). Intranasal administration of codeine is more effective than other routes of administration, because it permits absorption of codeine directly into the central nervous system, bypassing the metabolic enzymes present in the circulation, the gastrointestinal tract, and liver. Moreover, intranasal formulations of codeine may be conveniently and painlessly self-administered by the patient. Intranasal administration can be employed at far lower doses than oral administration, thereby allowing a decreased incidence of side effects.

According to the present invention, codeine may be administered either as a free base, or in the form of a pharmaceutically acceptable salt thereof. Pharmaceutically acceptable salts of the compounds of formula (I) which contain a basic center are, for example, non-toxic acid addition salts formed with inorganic acids such as hydrochloric, hydrobromic, sulphuric and phosphoric acid, with organo-carboxylic acids, for example, gluconate or with organo-sulphonic acids, for example, mesylate. Compounds of the formula (I) can also provide pharmaceutically acceptable metal salts, in particular non-toxic alkali metal salts, with bases adjusted for the desired pH. Examples include sodium and potassium salts.

A still further aspect of this invention is a pharmaceutical composition of matter that comprises codeine, or derivatives thereof, as described above, and/or pharmaceutically acceptable salts thereof, and pharmaceutically acceptable carriers therefor.

For therapeutic use in the prevention or treatment of pain or cough, codeine or salts thereof, can be conveniently administered in the form of a pharmaceutical composition containing codeine, or its salt, and a pharmaceutically acceptable carrier therefor. Typically, the carrier may be a liquid, solution, gel, or combinations thereof. In a preferred embodiment, the carrier is a pharmaceutically acceptable aqueous solution. Such compositions may require the use of one or more solubilizing agents to both effect dissolution of the drug(s) and/or keep them in aqueous solution. Suitable applications of solubilizing agents are exemplified below. Compositions according to the present invention may be prepared in accordance with accepted pharmaceutical practice, for example, as described in *Remington's Pharmaceutical Sciences*, seventeenth edition, ed. Alfonso R. Gennaro, Mack Publishing Company, Easton, Pa., Eighteenth edition (1990), which is hereby incorporated by reference.

Codeine or its salt may be formulated together with the carrier into any desired unit dosage form. Unit dosage forms such as solutions, suspensions, and water-miscible semisolids are particularly preferred.

Each carrier must be "acceptable" in the sense of being compatible with the other ingredients in the formulation and not injurious to the patient. The carrier must be biologically acceptable and inert. In most cases, suitable buffers are included in the carriers to maintain the pH within the limits required to keep the drugs in solution. For example, for drugs containing a basic center, the solutions are buffered in the acidic pH range (approximately 2 to 6), and for drugs containing an acidic center, the solutions are buffered in the alkaline pH range (approximately 8 to 12). To prepare formulations suitable for intranasal administration, solutions and suspensions are sterilized and are preferably isotonic to blood.

In formulating a composition according to the present invention for the treatment of pain, other drugs used in the treatment of pain may also be included. Such additional drugs include, but are not limited to, opioid analgesics, nonopioid analgesics, and antidepressants.

In formulating a composition according to the present invention for the treatment of cough, other drugs used in the treatment of cough may also be included. Such additional drugs include, but are not limited to, antitussive compounds, opioid analgesics, nonopioid analgesics, cough suppressants, and expectorants. Preferred opioid analgesics for use in the present invention in addition to codeine include, but are not limited to, oxycodone, morphine, hydromorphone, levorphanol, methadone, meperidine, butorphanol, fentanyl, and pharmaceutically acceptable salts thereof. Preferred nonnarcotic analgesics for use in the present invention include, but are not limited to, acetylsalicylic acid and pharmaceutically acceptable salts thereof. Preferred narcotic cough suppressants include, but are not limited to, drocode, hydrocodone, oxycodone, and pharmaceutically acceptable salts thereof. Preferred nonnarcotic cough suppressants for use in the present invention include, but are not limited to, benzonatate, carbetapentane, chlophedianol, dextromethorphan, noscapine, pipazethate, benzobutamine, bromohexine, guaiapate, guaiaphenesin, homoarylamine, pemerid, suxemerid, and pharmaceutically acceptable salts thereof.

According to the present invention, the term "patient" will encompass any mammal requiring treatment with codeine, or derivatives thereof, particularly a human patient suffering from pain and/or cough.

The dosage of codeine or pharmaceutically acceptable salts thereof in the compositions of the invention will vary depending on several factors, including, but not limited to, the age, weight, and species of the patient, the general health of the patient, the severity of the symptoms, whether the composition is being administered alone or in combination with other agents, the incidence of side effects and the like. The desired dose may be administered as needed, and may be administered repeatedly over a period of months or years. Higher and lower doses may also be administered. A major advantage of the present invention is the extremely rapid onset of response, which enables the physician to adjust the dose to produce only the desired effects and nothing more, thereby optimizing drug use and minimizing side-effects.

The daily dose may be adjusted taking into account, for example, the above-identified variety of parameters. Typically, codeine may be administered in an amount of up to about 60 mg/dose. Preferably, the amount of codeine administered will not exceed 30 mg/dose. However, other amounts may also be administered, in particular, much smaller amounts of codeine will be required when administered intranasally, in accordance with the present invention.

While it is possible for the active ingredient to be administered alone, as noted above, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients in a pharmaceutical composition. Other therapeutic agents suitable for use herein are any compatible drugs that are effective by the same or other mechanisms for the intended purpose, or drugs that are complementary to those of the present agents. Such additional drugs include, but are not limited to, opioid analgesics, nonopioid analgesics, antianxiety drugs, antidepressant drugs, antitussive drugs, and expectorants. The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

Having now generally described this invention, the same will be better understood by reference to certain specific examples, which are included herein for purposes of illustration only and are not intended to be limiting of the invention or any embodiment thereof, unless so specified. Set forth below are examples of experimental procedures designed to demonstrate the features of this invention in animal models, and examples of pharmaceutical dosage forms that embody and illustrate its reduction to practice.

EXAMPLE 1: NASAL SPRAY SOLUTION (FOR PAIN)

| | |
|---|---|
| Codeine phosphate | 30 g |
| 0.05M Phosphate buffer, pH 4.4 | 300 ml |

The codeine is dissolved in the phosphate buffer and pH of the solution is readjusted to 4.4 if necessary. The solution is placed in a nasal administrator designed to deliver 100 $\mu$l of spray for each application. One spray in each nostril will deliver a total of 20 mg of codeine phosphate.

EXAMPLE 2: NASAL GEL (AQUEOUS, FOR PAIN)

| | |
|---|---|
| Codeine sulfate | 10 g |
| Methocel | 3 g |
| 0.05M Acetate buffer, pH. 4.4 | 100 g |

Approximately 70 ml of the acetate buffer is heated to 80° C. and the methocel is dispersed in it with stirring. The codeine sulfate is dissolved in 30 ml of the acetate buffer at 80° C. and the solution is mixed with the methocel dispersion. The resultant mixture is allowed to stand at room temperature for 3 hours. The gel is placed in an ointment tube equipped with a fine orifice and is applied in the nasal nares with a finger or cotton tipped applicator.

EXAMPLE 3: NASAL SPRAY SOLUTION (ANTITUSSIVE)

| | |
|---|---|
| Codeine phosphate | 15 mg |
| 0.05M Phosphate buffer, pH 4.4 | 300 ml |

The codeine phosphate is dissolved in the phosphate buffer and the pH of the solution is readjusted to 4.4, if necessary. The solution is placed in a nasal administrator designed to deliver 100 $\mu$l of spray for each application. One spray in each nostril will deliver a total of 10 mg of codeine phosphate.

EXAMPLE 4: ABSORPTION OF CODEINE FROM THE NASAL CAVITY OF THE RAT— PENETRATION INTO THE PLASMA AND BRAIN (CSF)

The absorption of codeine into the blood of rats and its penetration into the brain or cerebrospinal fluid (CSF) following intranasal and intravenous administration of a solution of codeine phosphate in normal saline was studied using an in vivo experimental technique described by Hussain, et al (References 33 and 37, International Publication Number: WO 97/16181, May 9, 1997, which is incorporated herein by reference). A diagram of the experimental technique is shown in FIG. 12 of that application.

Plasma and CSF levels of codeine were assayed using the following HPLC method:

One hundred $\mu$L of rat plasma was treated with 100 $\mu$L of acetonitrile to precipitate the proteins. This mixture was centrifuged for 5 minutes at 5,000×g. The clear supernatant was injected onto the HPLC column.

The HPLC system included the following:
Column: Altex 5 micron Ultrasphere, 4.6 mm×25 cm
Mobile Phase: Acetonitrile: 0.01 M Acetate buffer (pH 4.0)–50:50
Flow Rate: 1 ml/min
Detection: UV@240 nm
Retention Time: 7.6 min
Standard Curve: See FIG. 1

Results

The plasma levels found in the rat nasal and intravenous administration studies are shown in Table I and FIG. 2. These results show that codeine is rapidly and completely absorbed following intranasal (IN) administration compared with intravenous (IV) administration. The AUC (area under the curve) following 5 mg/kg of codeine administered intranasally is roughly half that following 10 mg/kg IN, showing that there is no saturation of the absorption process at these dose levels.

TABLE I

Plasma Concentrations (μg/mL) of Codeine in Rats following Intravenous and Intranasal Administrations in Rats (n = 3)

| Time (min) | IV (10 mg/kg) | | IN (5 mg/kg) | | IN (10 mg/kg) | |
|---|---|---|---|---|---|---|
| | Mean | s.d. | Mean | s.d | Mean | s.d. |
| 0 | 19.40 | 1.60 | 0.00 | 0.00 | 0.00 | 0.00 |
| 2 | 9.40 | 0.70 | 0.84 | 0.32 | 1.40 | 0.08 |
| 5 | 5.20 | 0.16 | 2.88 | 0.04 | 5.10 | 1.00 |
| 10 | 2.70 | 0.72 | 3.15 | 0.20 | 7.62 | 0.58 |
| 20 | 2.04 | 0.64 | 2.24 | 0.30 | 3.32 | 0.50 |
| 40 | 1.22 | 0.20 | 0.60 | 0.20 | 1.42 | 0.42 |
| 60 | 0.86 | 0.06 | 0.56 | 0.10 | 1.10 | 0.18 |

AUC (0 to 60) 147.6 mg/mL/min 88.5 mg/mL/min 170.3 mg/mL/min
BIOAVAILABILITY = [AUC IV]/[AUC IN] = 170.3/147.6 = 115%

To study the penetration of codeine into the CSF or brain following IN administration, three groups of three rats were dosed as follows: 10 mg/kg IV, 5 mg/kg IN, and 10 mg/kg IN. At 60 minutes post-dose, the rats were sacrificed, and the CSF (0.1 ml) was recovered and injected directly onto the HPLC column.

The results are shown in Table II. These results were unexpected because the levels were much higher for 5 mg/kg administered intranasally than for 10 mg/kg administered intravenously. The results suggest that codeine penetrates from the nasal cavity directly into the CSF and/or brain of the rat.

TABLE II

Cerebrospinal Fluid (CSF) Concentrations (mg/mL) of Codeine in Rats 60 minutes following Intravenous (IV) or Intranasal (IN) Administration

| Animal Number | IV 10 mg/kg | IN 10 mg/kg | IN 5 mg/kg |
|---|---|---|---|
| 1 | 1.9 | 4.2 | 3.0 |
| 2 | 1.7 | 4.0 | 3.5 |
| 3 | 1.1 | 6.4 | 2.0 |
| Mean ± s.d. | 1.6 + 0.42 | 4.9 ± 1.3 | 2.8 ± 0.8 |

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A method for rapidly and reliably delivering codeine to the systemic circulation of a patient for the prevention or treatment of pain comprising intranasally administering an effective amount of codeine, or a pharmaceutically acceptable salt thereof to a patient in need of such prevention or treatment.

2. A method according to claim 1, wherein the pharmaceutically acceptable salt of codeine is codeine sulfate.

3. A method according to claim 1, wherein the pharmaceutically acceptable salt of codeine is codeine phosphate.

4. A method according to claim 1, wherein the pharmaceutically acceptable salt of codeine is codeine mesylate.

5. A method according to claim 1, wherein the codeine is provided in the form of a pharmaceutical composition comprising codeine and a pharmaceutically acceptable carrier therefor.

6. A method according to claim 5, wherein the carrier is aqueous.

7. A method according to claim 5, wherein the composition further comprises another active compound selected from the group consisting of opioid analgesics, nonopioid analgesics, and antidepressants.

8. A method according to claim 7, wherein the opioid analgesic is selected from the group consisting of oxycodone, morphine, hydromorphone, levorphanol, methadone, meperidine, butorphanol, fentanyl, and pharmaceutically acceptable salts thereof.

9. A method according to claim 7, wherein the nonopiod analgesic is selected from the group consisting of acetylsalicylic acid and pharmaceutically acceptable salts thereof.

10. A method according to claim 7, wherein the antidepressant is selected from the group consisting of doxepin, amitryptiline, imipramine, nortriptyline, desipramine, and pharmaceutically acceptable salts thereof.

11. A method for rapidly and reliably delivering codeine to the systemic circulation of a patient for the prevention or treatment of cough comprising intranasally administering an effective amount of codeine, or a pharmaceutically acceptable salt thereof to a patient in need of such prevention or treatment.

12. A method according to claim 11, wherein the pharmaceutically acceptable salt of codeine is codeine sulfate.

13. A method according to claim 11, wherein the pharmaceutically acceptable salt of codeine is codeine phosphate.

14. A method according to claim 11, wherein the pharmaceutically acceptable salt of codeine is codeine mesylate.

15. A method according to claim 11, wherein the codeine is provided in the form of a pharmaceutical composition comprising codeine and a pharmaceutically acceptable carrier therefor.

16. A method according to claim 15, wherein the carrier is aqueous.

17. A method according to claim 15, wherein the composition further comprises another active compound selected from the group consisting of opioid analgesics, nonopiod analgesics, cough suppressants, and expectorants.

18. A method according to claim 17, wherein the opioid analgesic is selected from the group consisting of oxycodone, morphine, hydromorphone, levorphanol, methadone, meperidine, butorphanol, fentanyl, and pharmaceutically acceptable salts thereof.

19. A method according to claim 17, wherein the nonopiod analgesic is selected from the group consisting of acetylsalicylic acid and pharmaceutically acceptable salts thereof.

20. A method according to claim 17, wherein the cough suppressant is a narcotic cough suppressant selected from the group consisting of drocode, hydrocodone, oxycodone, and pharmaceutically acceptable salts thereof.

21. A method according to claim 17, wherein the cough suppressant is a nonnarcotic cough suppressant selected from the group consisting of benzonatate, carbetapentane, chlophediacol, dextromethorphan, noscapine, pipazethate, benzobutamine, bromohexine, guaiapate, homoarylamine, pemerid, suxemerid, and pharmaceutically acceptable salts thereof.

* * * * *